United States Patent [19]

Matson

[11] Patent Number: 5,666,948

[45] Date of Patent: Sep. 16, 1997

[54] ATTACHMENT FOR AEROSOL DEVICE FOR LARGE ANIMALS AND METHOD OF USE

[75] Inventor: Charles J. Matson, Stillwater, Minn.

[73] Assignee: Minnesota Mining and Manufacturing Company, St. Paul, Minn.

[21] Appl. No.: 395,177

[22] Filed: Feb. 27, 1995

Related U.S. Application Data

[63] Continuation of Ser. No. 269,635, Jul. 1, 1994, abandoned, which is a continuation of Ser. No. 17,137, Feb. 12, 1993, abandoned.

[51] Int. Cl.$^6$ .................. A61M 11/00; A61M 15/00; A61M 16/10
[52] U.S. Cl. .................. 128/200.23; 128/203.12; 128/207.18
[58] Field of Search .................. 128/200.14, 200.23, 128/200.24, 203.12, 203.14, 203.15, 203.23–203.25, 204.11, 204.12, 207.14, 207.18; 604/26, 37, 94, 132, 142, 275

[56] References Cited

U.S. PATENT DOCUMENTS

| | | | |
|---|---|---|---|
| 128,257 | 6/1872 | Snyder . | |
| 991,022 | 5/1911 | Rees et al. . | |
| 1,378,481 | 5/1921 | Mobley | 128/200.23 |
| 1,856,811 | 5/1932 | Inaki . | |
| 1,935,973 | 11/1933 | Altmann | 128/200.23 |
| 1,988,979 | 1/1935 | Campbell | 128/200.23 |
| 2,255,833 | 9/1941 | Taylor . | |
| 2,434,875 | 1/1948 | Turnbull et al. . | |
| 2,582,529 | 1/1952 | Curry et al. . | |
| 2,612,894 | 10/1952 | Akins . | |
| 2,829,642 | 4/1958 | De Melfy . | |
| 2,843,119 | 7/1958 | Glasser . | |
| 2,946,332 | 7/1960 | Sacks . | |
| 3,007,613 | 11/1961 | Tygard | 128/200.23 |
| 3,066,669 | 12/1962 | De Melfy . | |
| 3,415,248 | 12/1968 | Scott . | |
| 3,648,695 | 3/1972 | Bowen | 128/225 |
| 3,820,698 | 6/1974 | Franz | 222/205 |
| 3,857,423 | 12/1974 | Ronca, Jr. | 141/5 |
| 3,915,165 | 10/1975 | Rambosek et al. | 128/145.8 |
| 4,106,503 | 8/1978 | Rosenthal et al. | 128/194 |
| 4,122,841 | 10/1978 | Rock et al. | 128/2 Z |
| 4,143,658 | 3/1979 | Rambosek et al. | 128/184 |
| 4,300,545 | 11/1981 | Goodnow | 128/200.14 |
| 4,343,304 | 8/1982 | Hickmann | 128/200.14 |
| 4,381,773 | 5/1983 | Goodnew et al. | 128/200.14 |
| 4,410,320 | 10/1983 | Dykstra et al. | 604/27 |
| 4,432,758 | 2/1984 | Finegold | 604/104 |
| 4,546,768 | 10/1985 | Ferierabend | 128/200.16 |
| 4,678,106 | 7/1987 | Newell et al. | 128/200.23 |
| 4,722,334 | 2/1988 | Blackmer et al. | 128/203.16 |
| 4,782,832 | 11/1988 | Trimble et al. | 128/207.18 |
| 4,790,305 | 12/1988 | Zoltan et al. | 128/200.23 |
| 4,801,093 | 1/1989 | Brunet et al. | 239/490 |
| 4,908,382 | 3/1990 | Blanco | 514/471 |
| 4,953,546 | 9/1990 | Blackmer et al. | 128/203.16 |
| 5,053,022 | 10/1991 | Bryant et al. | 604/278 |
| 5,062,423 | 11/1991 | Matson et al. | 128/207.15 |

FOREIGN PATENT DOCUMENTS

| | | | |
|---|---|---|---|
| 0 537 991 A2 | 4/1993 | European Pat. Off. | 128/200.23 |
| 166171 | 12/1905 | Germany . | |
| 218538 | 10/1989 | New Zealand . | |
| 174811 | 7/1994 | New Zealand . | |
| 6707 | of 1909 | United Kingdom . | |

OTHER PUBLICATIONS

"Protective Studies with Group A Streptococcal M Protein Vaccine", by Alessandri et al., The Journal of Infectious Diseases, vol. 158, No. 6, 1978 (7 pages)—pp. 712–718.

(List continued on next page.)

*Primary Examiner*—Kimberly L. Asher
*Attorney, Agent, or Firm*—Gary L. Griswold; Walter N. Kirn; Jeffrey J. Hohenshell

[57] ABSTRACT

An aerosol generating device and a conduit for use with the aerosol generating device are disclosed. The conduit and aerosol generating device may be used in a method for administering an aerosol to a large animal, such as a horse.

40 Claims, 9 Drawing Sheets

OTHER PUBLICATIONS

"Protective Studies with a Group A Streptococcal M Protein Vaccine", by Polly et al., The Journal of Infectious Diseases, vol. 131, No. 3, 1975 (8 pages)–Pp. 217–224.

Casarett and Doull's Toxicology, The Basic Science of Poisons, Fourth Edition, by Amdur et al., (3 pages) including p. 391.

"Deposition and Fate of Inhaled Pharmacologic Aerosols", by Brain et al., Spector SL (ed): Provocative Challenge Procedures: Background and Methodology, Futura Publishing Company, Inc., Mount Kisco, NY, 1989 (4 pages).

"Proceedings of the Inhalation Toxicology and Technology Symposium", Sponsored by The Upjohn Company, Kalamazoo, Michigan, Oct. 23–24, 1980, edited by Basil K. J. Leong, (16 pages).

"Pharmaceutical Inhalation Aerosol Technology", edited by Anthony J. Hickey, University of Illinois, Chicago, Illinois, (8 pages), 1992.

"The Viscera of the Domestic Mammals", Second Revised Edition, by August Schummer, Richard Nickel and Wolfgang Otto Sack, 1979 (13 pages).

"Aerosols", Chapter 92, Philadelphia College of Pharmacy and Science, by John J. Sciarra, and Anthony J. Cutie (20 pages).

"Encyclopedia of Chemical Technology", Third Edition, vol. 21 by John Wiley & Sons (19 pages).

"Airway Reactivity in Ponies with Recurrent Airway Obstruction (Heaves)", by F. J. Derksen et al., American Physiological Society, 1985 (7 pages).

"Aerosol Pirbuterol: Brochodilator Activity and Side Effects in Ponies with Recurrent Airway Obstruction (Heaves)", by F. J. Derksen et al., Equine Veterinary Journal, 1992 (6 pages).

"The Anatomy of the Domestic Animals", by Septimus Sesson, S.B., V.S., D.V.Sc., Third Edition, 1941 (4 pages).

"Mucosal Nasopharyngeal Immune Responses of Horses to Protein Antigens of Streptococcus equi", by Jorge E. Galan and John F. Timoney, Infection and Immunicty, vol. 47., No. 3., pp. 623–628, 1985 (21 pages).

Four sheets which show horse anatomy.

Photocopy of package: Jen–Sal and directions for vaccinating intranasally (2 pages).

Package insert with directions and precautions for *Feline Infectious Peritonitis Vaccine*, published by SmithKline Beecham, 915 75-4643–02, printed in U.S.A., SmithKline Beecham Animal Health, Div. of SmithKline Beecham Corp., West Chester, PA 98380, U.S.A. (2 pages).

Pamplet entitled "A Quick Squeeze For Canine Cough Protection" by Shering–Plough Animal Health, 1992, Schering Corporation, U.S.A., SPIV–INT–37. (4 pages).

*Naramune-2*™ Product description, p. 602 of reference book describing vaccines.

Attachment A, Photograph of a Device For Delivering Canine Parainfluenza Bordetella Bronchiseptica Vaccine; available from Schering Plough of Omaha, Nebraska. The device was shown to the Examiner during a recent interview for this case.

File History of U.S. Patent No. 4,300,545.

File History of U.S. Patent No. 4,381,773.

2 Page Copy of Box for Canine Parainfluenza Bordetella Bronchiseptica Vaccine available from Schering Plough of Omaha, Nebraska.

5,666,948

ATTACHMENT FOR AEROSOL DEVICE FOR LARGE ANIMALS AND METHOD OF USE

This application is a continuation of U.S. patent application Ser. No. 08/269,635, filed Jul. 1, 1994, now abandoned which was a continuation of U.S. patent application Ser. No. 08/017,137 filed Feb. 12, 1993, now abandoned.

TECHNICAL FIELD

This invention relates generally to aerosol delivery methods and devices, and more particularly to an easily insertable apparatus for delivering an aerosol medicament to a large animal, such as a horse, to treat various conditions or ailments.

BACKGROUND OF THE INVENTION

Large animals suffer from a variety of diseases or illnesses which vary in severity from life threatening to minor ailments. Even minor illnesses may result in consequences (e.g. weight loss) which may adversely affect the economic value of the animal. For example, some horses suffer from chronic obstructive pulmonary disease (see, e.g., F. J. Derksen et al., Airway Reactivity in Ponies with Recurrent Airway Obstruction (Heaves), Journal of Applied Physiology 58(2): 598–604 (1985)). Obstructive lung disease, like asthma, is characterized by acute episodes of airway obstruction due to constriction of airway muscles. The resulting bronchoconstrictive state can result in serious adverse health consequences for the horse due to clinically compromised breathing.

The art is replete with devices and methods for delivering medicaments, vaccines or therapeutic agents to large animals for treatment or cure of diseases or illnesses. Obstructive lung disease in horses has been treated by injecting relatively large doses of medication directly into the blood stream of the horse. Large doses (relative to an aerosol dose) of the medication are often required since the medication has not been specifically targeted to the lungs of the horse. Those larger doses increase the risk of undesirable side effects.

Delivering a medicament or therapeutic agent in aerosol form is becoming increasingly popular. For example, U.S. Pat. Nos. 3,915,165 and 4,143,658 describe intratracheal injection systems for injecting dry medicaments in a gaseous suspension into the trachea of an animal in order to treat pneumonia. That system includes a needle (e.g., a catheter) that is inserted into the lumen of the trachea of the animal by puncturing the wall of the trachea. The dry medicaments are then administered through the catheter. Also, a pirbuterol aerosol has been administered through a tube inserted into a chronic tracheostoma in a horse (see, F. J. Derksen et al., Aerosol Pirbuterol: Bronchodilator Activity and Side Effects in Ponies With Recurrent Airway Obstruction (Heaves), Equine Veterinary Journal, 24 (2), pages 107–112 (1992)).

U.S. Pat. No. 5,062,423 is directed to a method of end apparatus for delivering a dose of an aerosol medicament to the lungs of a large animal such as a horse. A distal end of an endotracheal-like nasal tube is inserted via a nostril of the horse into its nasal-pharyngeal cavity. The nasal tube prevents aerosolized medicaments from becoming entrained or adsorbed onto the tissue between the opening of the nostril and nasal-pharyngeal cavity of the horse. However, insertion of the nasal tube calls for the operator to place the distal end of the tube in the nasal-pharyngeal cavity of the horse. Such precise placement of the nasal tube may be a difficult task to perform repeatedly.

SUMMARY OF THE INVENTION

This invention provides an apparatus for administering an aerosol to a large animal, such as a horse. The apparatus comprises a conduit that is inserted into the nostril of the horse. The conduit is used with an aerosol generating device which preferably generates a respirable aerosol.

The conduit has inner surfaces defining a lumen, outer surfaces, a proximal end, a distal end having an outlet, and connecting surfaces for connecting the conduit to the aerosol generating device.

The conduit has a length which affords locating the outlet in the nasal passageway of the horse. When the large animal comprises a horse, the nasal passageway includes a nasal diverticulum. The conduit should have a sufficient length such that, when the conduit is fully inserted into the nostril, the orifice does not allow passage of the aerosol into the nasal diverticulum. As a result of the length of the conduit, the conduit is both easily insertable into the nostril of the horse and an effective mechanism for delivering a respirable aerosol. Additionally, the length of the conduit renders it less likely to irritate sensitive mucosal membranes of the nasal passageway.

Preferably, the outer surfaces of the conduit are irregular shaped to conform to the irregular shaped surfaces of the horse's nasal passageway. When the outer surfaces conform to the nasal passageway, the conduit is easily placed in the nasal passageway in the proper orientation. Also preferably, the outer surfaces comprise sealing surfaces adapted to abut the tissue surrounding the nostril so that substantially all of the inspiratory airflow through that nostril is directed through the lumen of the conduit.

Once inserted into the nostril, the conduit affords passage of the aerosol in generally the same direction as the inspiratory airflow through the nostril to beneficially entrain the aerosol in the inspiratory airflow. In particular, after insertion of the conduit, the inspiratory airflow through the nasal passageway at the location of the outlet defines a first direction, and the conduit affords passage of the aerosol through the outlet in a direction that is generally parallel to the first direction.

The conduit preferably has a generally bulbous first section and a second section. The outlet is situated in the second section and the connecting surfaces are situated in the first section. The cross-sectional area of a cross-section in the first section is generally larger than the cross-sectional area of a cross-section in the second section so that inner surfaces of the first section of the conduit form an expansion chamber. The inclusion of an expansion chamber is believed to be particularly desirable when a respirable aerosol is delivered.

The conduit and aerosol generating device described above may be used in a method of administering a respirable aerosol to a large animal, also according to the present invention. The method comprises the steps of (1) providing an aerosol generating device, (2) providing a conduit, (3) connecting the conduit to the aerosol generating device so that the outlet of the conduit is in fluid communication with the aerosol generating device, (4) inserting the distal end of the conduit into the nostril of the large animal; and (5) then actuating the aerosol generating device to deliver the respirable aerosol.

BRIEF DESCRIPTION OF THE DRAWING

The present invention will be further described with reference to the accompanying drawing wherein like reference numerals refer to like parts in the several views, and wherein.

DETAILED DESCRIPTION OF PREFERRED EMBODIMENTS

Figure 1:
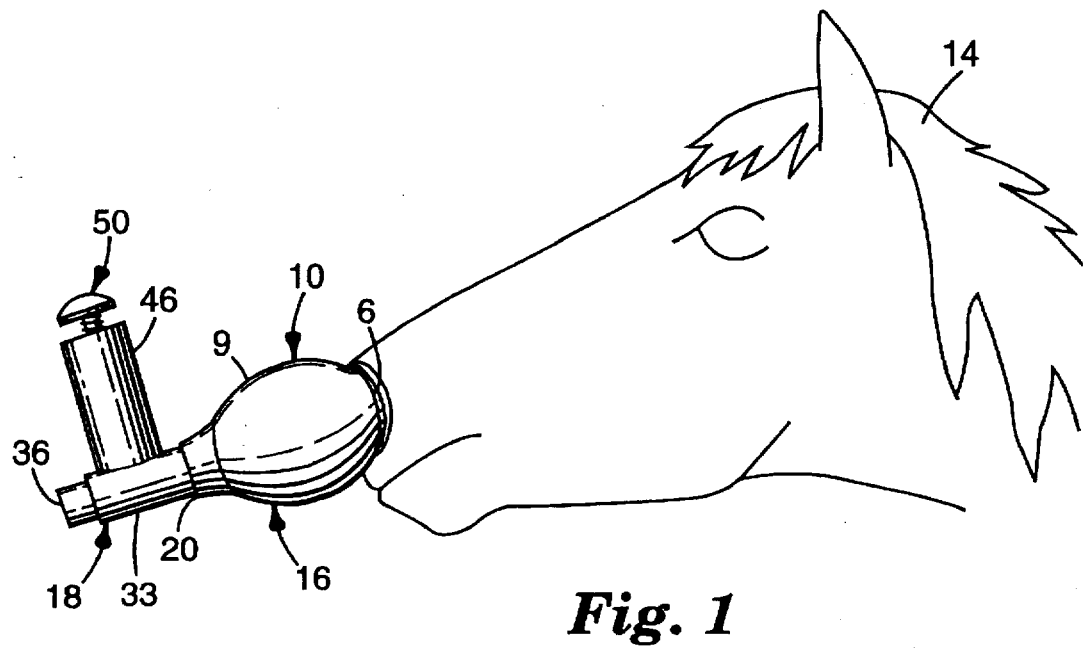
FIG. 1 is a side view of a head of a horse and the apparatus which includes the conduit and aerosol generating device according to the present invention.
Figure 2:
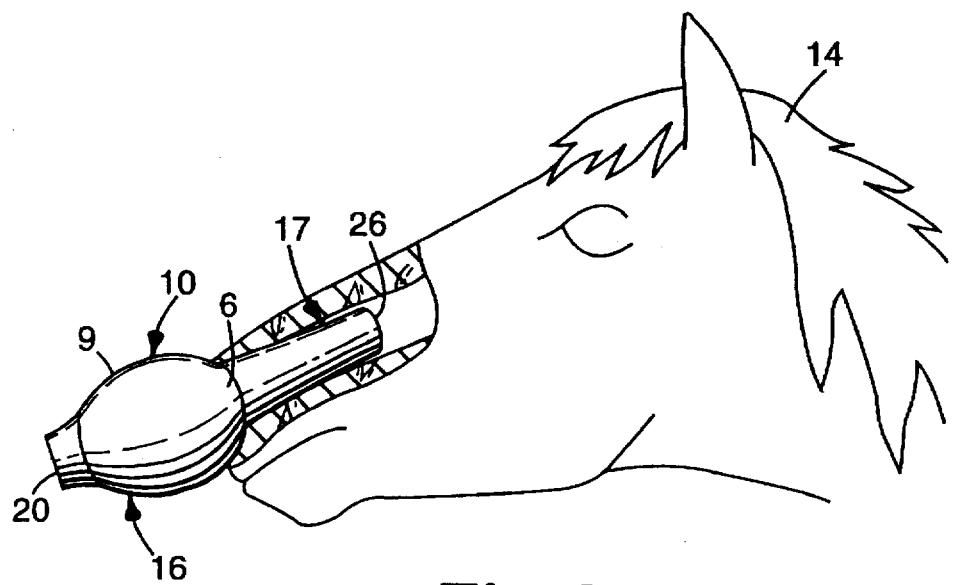
FIG. 2 is a side view similar to FIG. 1 with the aerosol generating device omitted and with portions being broken away to illustrate placement of the conduit of the present invention.

Referring now to FIGS. 1 through 7 and 9 of the drawing, there is shown one embodiment of a conduit according to the present invention generally designated by reference character 10. As shown in FIGS. 1 and 2, portions of the conduit 10 are inserted into a nostril of the large animal, after which the conduit 10 may be used to administer an aerosol to the large animal.

As used herein, the phrase, "large animal" includes but is not limited to equidae, bovidae, cervidae, cetaceans and other domestic and wild non-primate mammalian species. Particular examples not intended to be limiting include horses, goats, cattle, deer, sheep and dolphins. The conduit 10 is particularly suitable for use with a horse 14. The phrase "large animal", however, specifically excludes humans.

The conduit 10 may be used with an aerosol generating device is for generating an aerosol. As used in this application, when used alone, the term "aerosol" is used broadly and means a gaseous suspension or solution of dispersed solid or liquid particles. As used herein, the term "aerosol" includes sprays, colloids, mists and respirable aerosols. The aerosol may be in suspension, solution or dry powder form. An aerosol may comprise a medicament, therapeutic agent, growth promotor, prophylactic agent or a nutritional agent. Examples of aerosols include medicaments, drugs and vaccines.

Preferably the aerosol generating device 18 generates a respirable aerosol which specifically targets the lungs of an animal. As used in this application, the phrase "respirable aerosol" means an aerosol having a component that is ultimately delivered to the lungs of the large animal, as opposed, for example, to an aerosol with droplets that are designed to be deposited on the surfaces of the animal's nasal passages and subsequently adsorbed onto the tissue of the nasal passages. Preferably, using the horse 14 as an example, the component will be delivered beyond the upper respiratory tract and to the peripheral lung field (e.g. the alveoli of the lung). Typically the component of a respirable aerosol medicament includes an appreciable amount of medicament particles having a size of less than about thirty (30) micrometers, and preferably less than about ten (10) micrometers when measured using a multistage cascade impactor (generally available from Anderson Samplers, of Atlanta, Ga.) according to the method described by Chowtan, Z. T. et al. in "Report and Recommendations of the USP Advisory Panel on Aerosols on the USP General Chapter <601> on Aerosols" Pharmacopeial Forum 1991; 17(2), Pps. 1703–1713. For purposes of this application, an "appreciable amount" of a respirable aerosol medicament means an amount capable of eliciting a therapeutic or physiological response, as opposed to a mere trace or negligible amount.

The conduit 10 has outer surfaces 9, a proximal end 20, a distal end 26 having an outlet O, and inner surfaces 11 which preferably afford passage of an aerosol generated by the aerosol generating device 18 through the conduit 10. The inner surfaces 11 define a lumen extending between the proximal 20 and distal 26 ends, and open to the outer surfaces 9 at the outlet O.

The conduit 10 also includes connecting surfaces preferably adjacent the proximal end 20 of the conduit 10. The connecting surfaces may be used to removably connect the conduit 10 to the aerosol generating device 18 so that the outlet O of the conduit 10 may be placed in fluid communication with the aerosol generating device 18.

The conduit 10 comprises first 16 and second 17 sections with the outlet O situated in the second section 17 and the connecting surfaces situated in the first section 16. The edge of the conduit 10 forming the distal end 26 is smoothly rounded in order to facilitate introduction of the conduit 10 into the nostril N of the horse 14 and to avoid irritating tissue.

Figure 7:
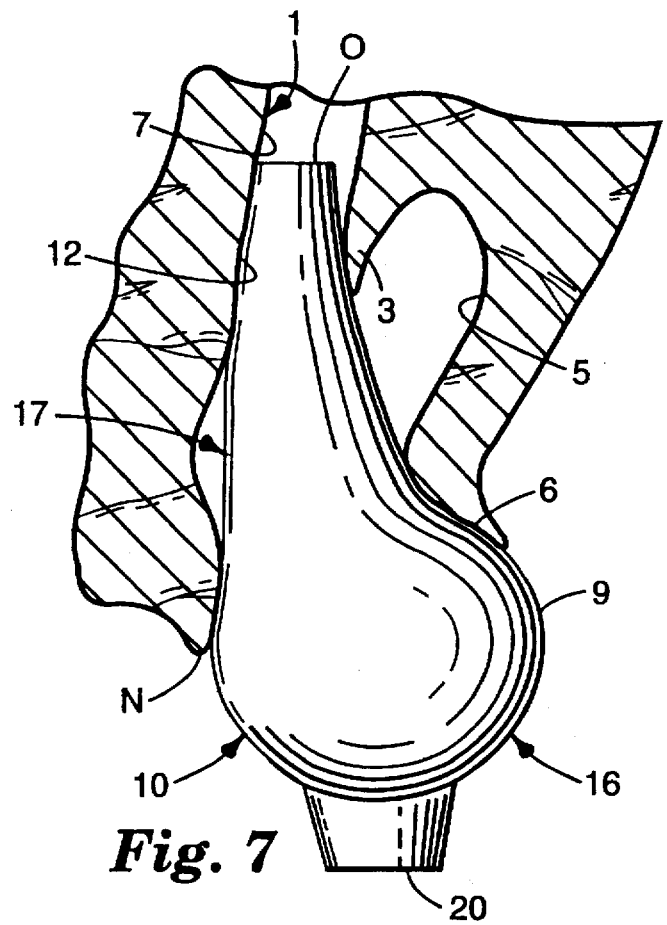
FIG. 7 is a schematic illustration of the position of the conduit of FIG. 5 within the nostril of a horse.

FIG. 7 is a schematic illustration of the conduit 10 positioned within the end of the respiratory passageway 1 of a horse 14. As schematically shown, the nasal passageway 1 of the horse 14 begins at the nostril N of the horse and includes the nasal diverticulum 5 and the ventral passage 7.

The conduit 10 has a length which affords locating the outlet in the nasal passageway of the large animal. As used in this application, the phrase "nasal passageway of the large animal" means those surfaces between (1) the outer end of the animal's nasal tract (e.g. the opening of the animal's nostril) and (2) the juncture of the nasal-pharyngeal cavity.

Locating the outlet O of the conduit 10 in the nasal passageway as opposed to the nasal-pharyngeal cavity is believed to facilitate convenient, efficient, and effective insertion of the conduit 10 into the nostril of the horse 14.

The conduit 10 should have a sufficient length such that, when fully inserted, the orifice O does not allow passage of the aerosol (e.g. a respirable medicament) into the nasal diverticulum 5 of the horse 14 (where a substantial amount of the medicament may be wasted, or where the uptake of the medicament may be substantially delayed). Preferably, when the conduit 10 is fully inserted into the nostril of the horse, the outlet O is located in the nasal vestibule and is bounded medially by the nasal septum, dorso-laterally by the alar fold and ventrally by nasal mucosa. The orifice O should not project excessively far into the nasal passageway to afford ease of insertion of the conduit 10 and to avoid irritating sensitive mucosal membrane tissue of the nasal passageway/cavity that may cause discomfort for the horse 14.

The outer surfaces 9 of the conduit 10 comprise sealing surfaces 6 adapted to abut the tissue surrounding the nostril N of the horse 14 such that substantially all of the inspiratory airflow through the nostril is directed through the lumen of the conduit 10. Additionally, the amount or degree of insertion of the conduit 10 into the nostril is limited by the sealing surface's 6 to avoid accidental over insertion or lodging of the conduit 10 in the nasal passageway.

The sealing surfaces 6 are preferably sized and shaped (e.g. the semi-spherical shape shown in the figures) to abut and cooperate with the socket-like opening of the horse nostril. However, optionally the sealing surfaces may comprise other shapes such as a frusto-conical shape so long as they generally conform to the surfaces.

The sealing surfaces 6 form a seal with a nostril so that substantially all of the inspiratory airflow through that nostril also flows through the conduit. Directing substantially all of the inspiratory airflow through the conduit is believed to beneficially entrain the aerosol into the inspiratory airflow to increase the likelihood that the aerosol will completely traverse the respiratory system of the animal and become entrained on the peripheral surfaces of the lung.

The outer surfaces 9 forming the first section 16 are preferably constantly curved to form a bulbous first section. Preferably, the first 16 and second 17 sections of the conduit 10 have cross-sections with arcuate portions which reflect the irregular shape of the conduit. Also preferably, the cross-sectional area of a cross-section in the first section 16 is generally larger than the cross-sectional area of a cross-section in the second section 17.

When an respirable aerosol is passed through the lumen of the conduit 10, the inner surfaces 11 of the first section 16 of the conduit 10 form an expansion chamber to afford expansion and maturation of conduit 10. The expansion chamber affords many potential advantages: (1) it allows particles or droplets generated by the aerosol generating device 18 that would not otherwise reach the lungs of the animal (e.g. large particles) to "drop out" of the aerosol, (2) it slows down the speed of the individual particles or droplets in the aerosol before they leave the conduit, and (3) if the aerosol generating device 18 utilizes a propellant, the expansion chamber allows some propellant to evaporate from the aerosol prior to leaving the conduit.

As an example not intended to be limiting, the conduit 10 should have an overall length L (see FIG. 6) of about 5.4 inches, a generally elliptical outlet O having a width of about 1.14 inches and a height of about 0.77 inches, a maximum outer diameter of about 2.64 inches in the first section, an opening adjacent the proximal end 20 having an inner diameter of about 0.875 inches, an axial length from the proximal end 20 to a point on the axis of the conduit 10 which defines the maximum outer (radial) diameter of about 1.95 inches, and a generally constant thickness of about 0.2 inches.

The aerosol-generating device 18 includes a canister 22 of the type for dispensing a metered dose of a medicament through a hollow stem 24. A metered dose is dispensed from such a canister 22 when a metering valve mechanism (not shown) is actuated, which typically occurs when the stem 24 is moved relative to the canister 22. For example, suitable canisters 22 are described in U.S. Pat. Nos. 4,819,834 and 3,738,542 (incorporated herein by reference). Canisters 22 of this type include a propellant and multiple doses of the medicament, which are discharged in predetermined standard amounts via a metering valve mechanism (not shown) actuated either by relative inward movement of the stem 24, or relative outward movement of the stem 24 following inward movement. Such metering valve mechanisms are typically designed to deliver a predetermined volume of the aerosol dose, for example, 50 or 63 microliters, each time the mechanism is actuated. Alternatively, the aerosol generating device may comprise a nebulizer or dry powder inhaler.

The connecting surfaces are connected to a means for connecting the conduit 10 to the canister 22. The means comprises a body 33 having an air passageway 34 in fluid communication with the lumen of the conduit 10, and an air opening 36. The body 33 is connected to the conduit 10 at end 60.

A stem receptacle 38 is provided in the body 33 outside and generally adjacent the air passageway 34 for receiving the stem 24 of the canister 22. A hollow tube 40 preferably extends generally transversely or laterally across the air passageway 34 from a portion of the wall of the passageway 34 adjacent the stem receptacle 38. The terms, "transversely" and "laterally" are used in the same manner as their use in U.S. Pat. No. 5,062,423.

The hollow tube 40 is in fluid communication with a hollow stem 24 received in the stem receptacle 38, and the stem receptacle 38 seals along the sides of the stem 24 so that a metered dose discharged from the canister 22 is forced into the hollow tube 40. The arrangement is such that, when the canister 22 is pushed toward the stem receptacle 38, the stem 24 is moved toward the canister 22 to actuate the metering valve mechanism and discharge a dose into the hollow tube 40.

An orifice 42 is provided in the hollow tube 40, and opens into the air passageway 34 from the bore of the tube 40 for delivering a metered aerosol dose into the inhalation air stream flowing through the air passageway 34. The orifice 42 preferably opens through the hollow tube 40 along the central longitudinal axis of the air passageway 34 in the direction toward the conduit 10 (rightwardly in FIG. 4), to facilitate entraining the aerosol medication in the air stream, while minimizing the amount of medication deposited along the walls of the air passageway 34 of the aerosol generating device 18. Preferably, the hollow tube 40 extends completely across the air passageway 34 and the orifice 42 is positioned along the midpoint of the hollow tube 40.

The hollow tube 40 may be formed of a narrow stainless steel tube (also 40) having an outside diameter of approximately 0.049 in. (1.2 mm), and an inside diameter of approximately 0.033 in. (0.81 mm), which is appropriate for preventing premature aerosolization of a metered dose inside the hollow tube 40. The orifice 42 preferably has a circular cross-section section of approximately 23 thousands of an inch (584 micrometers) diameter.

A canister housing 46 may be provided for securing canisters 22 (e.g. replacements) for operation of the aerosol-generating device 18. The canister housing 46 is detachably or "releasably" mountable on the body 33 of the aerosol-generating device 18 via, for example, a bayonet fastening mechanism illustrated generally at 48. Alternatively, the canister 22 may be simply slip fit to the body 33.

A triggering mechanism 50 may also be provided for moving the canister 22 toward the stem receptacle 38, thereby moving the stem 24 of the canister 22 toward the canister 22 to actuate the metering valve mechanism and discharge an aerosol dose into the hollow tube 40. The triggering mechanism 50 may include a push button 52 for releasably pressing the canister 22 toward the stem receptacle 38 to discharge a metered dose, and a resilient coil spring 54 pressing against both the push button 52 and the housing 46 to bias the push button 52 toward its ready position.

An air flow indicator is preferably mounted in the air passageway 34 of the body 33 to visibly, tactily or audibly indicate when a metered dose should be discharged from the canister 22 for optimum effect. For example, the indicator may include a vane 56 (FIG. 4) movable (pivotable) in response to air flow through the lumen of the conduit 10. A window 57 may be provided in the body 33 of the aerosol-generating device 18 so that the vane 56 may be observed visibly. Such a vane 56 may readily be adapted to generate an audible signal by striking the wall of the air passageway 34 when reduced pressure causes it to pivot.

Figure 3:
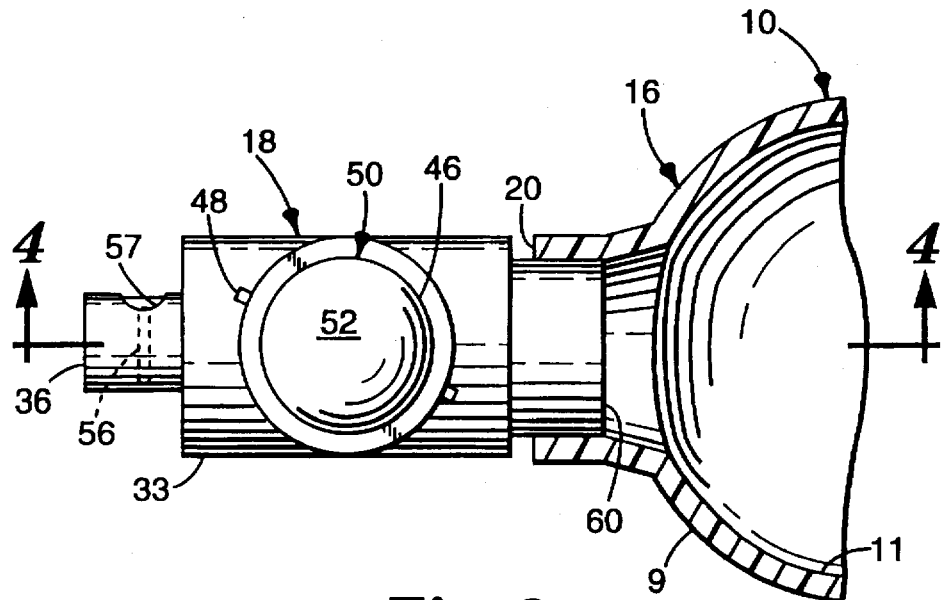
FIG. 3 is an enlarged top plan view of an aerosol-generating device used in conjunction with the conduit of FIG. 2 which illustrates portions of the conduit according to an aspect of the present invention with the rest of the conduit broken away.
Figure 4:
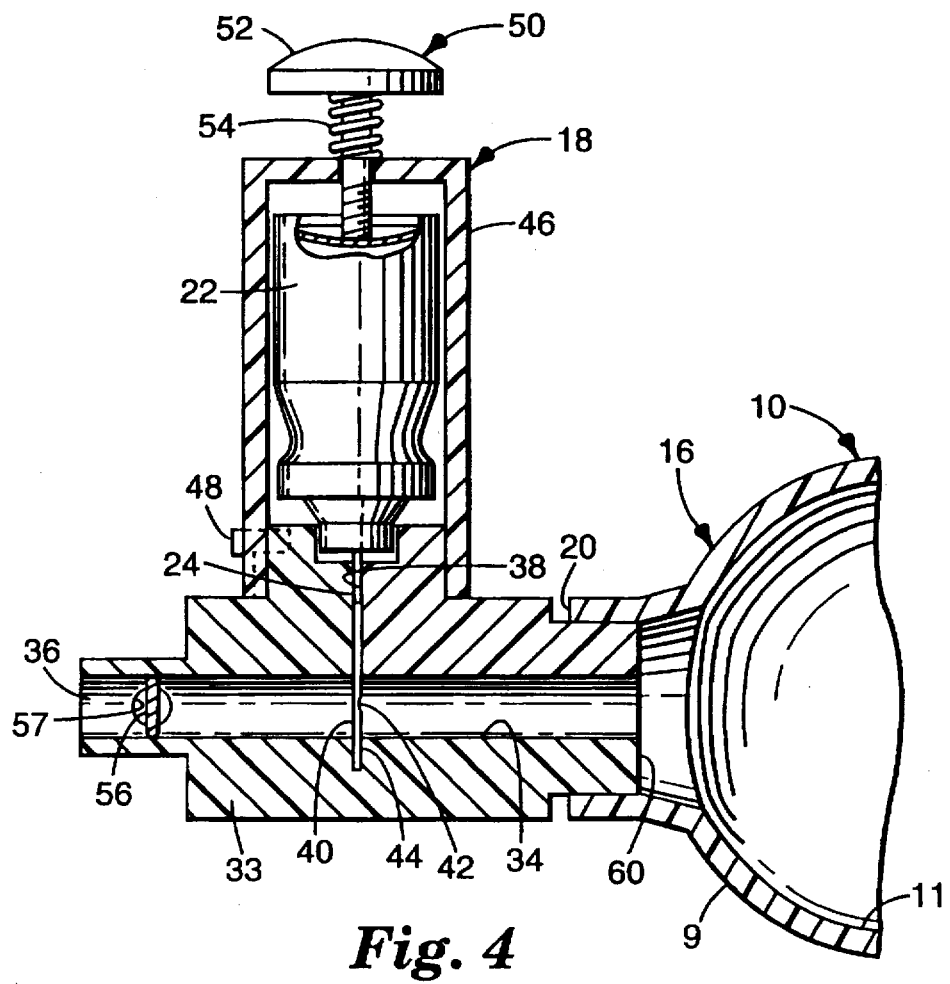
FIG. 4 is a cross-sectional view taken generally along line 4—4 of FIG. 3.
Figure 5:
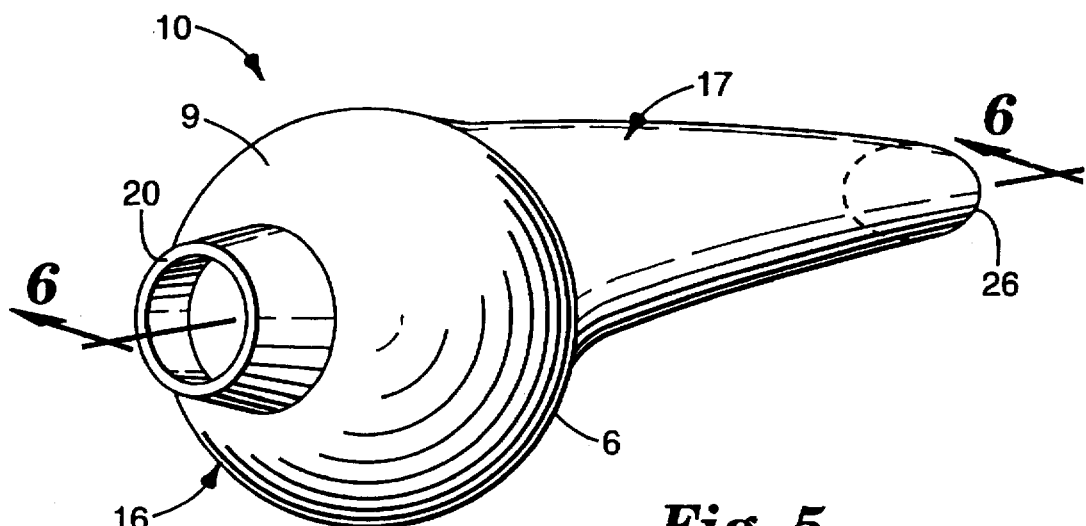
FIG. 5 is a perspective view of one embodiment of a conduit according to the present invention.
Figure 6:
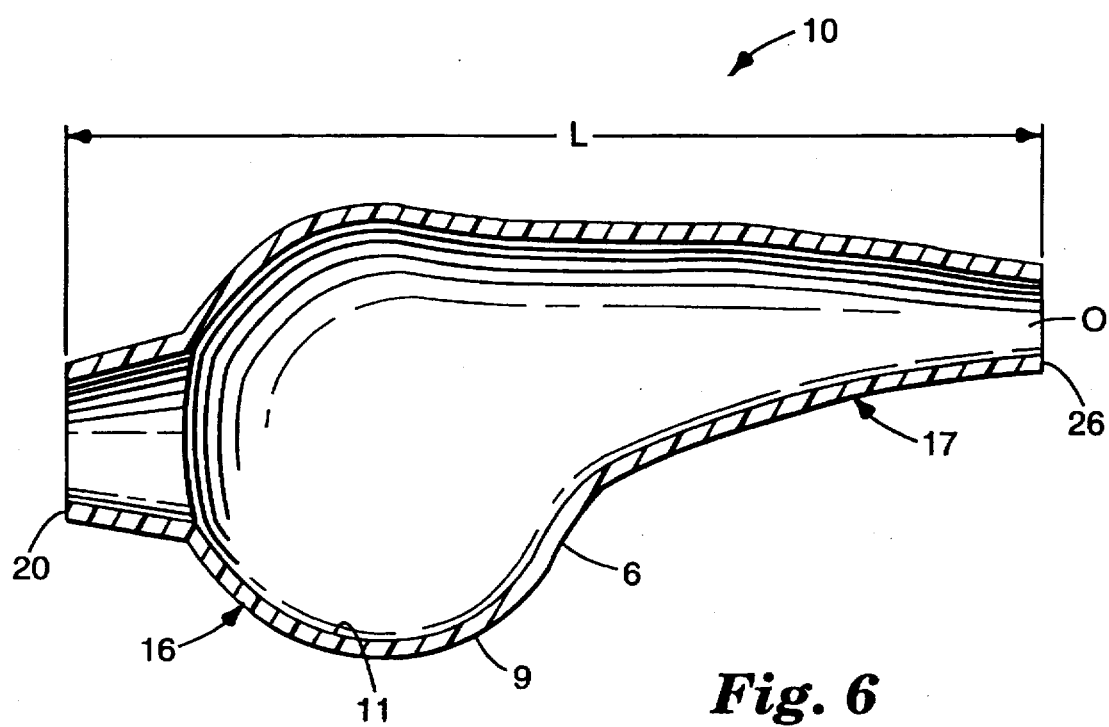
FIG. 6 is a sectional view of the conduit of FIG. 5 taken approximately along line 6—6 of FIG. 5.
Figure 11:
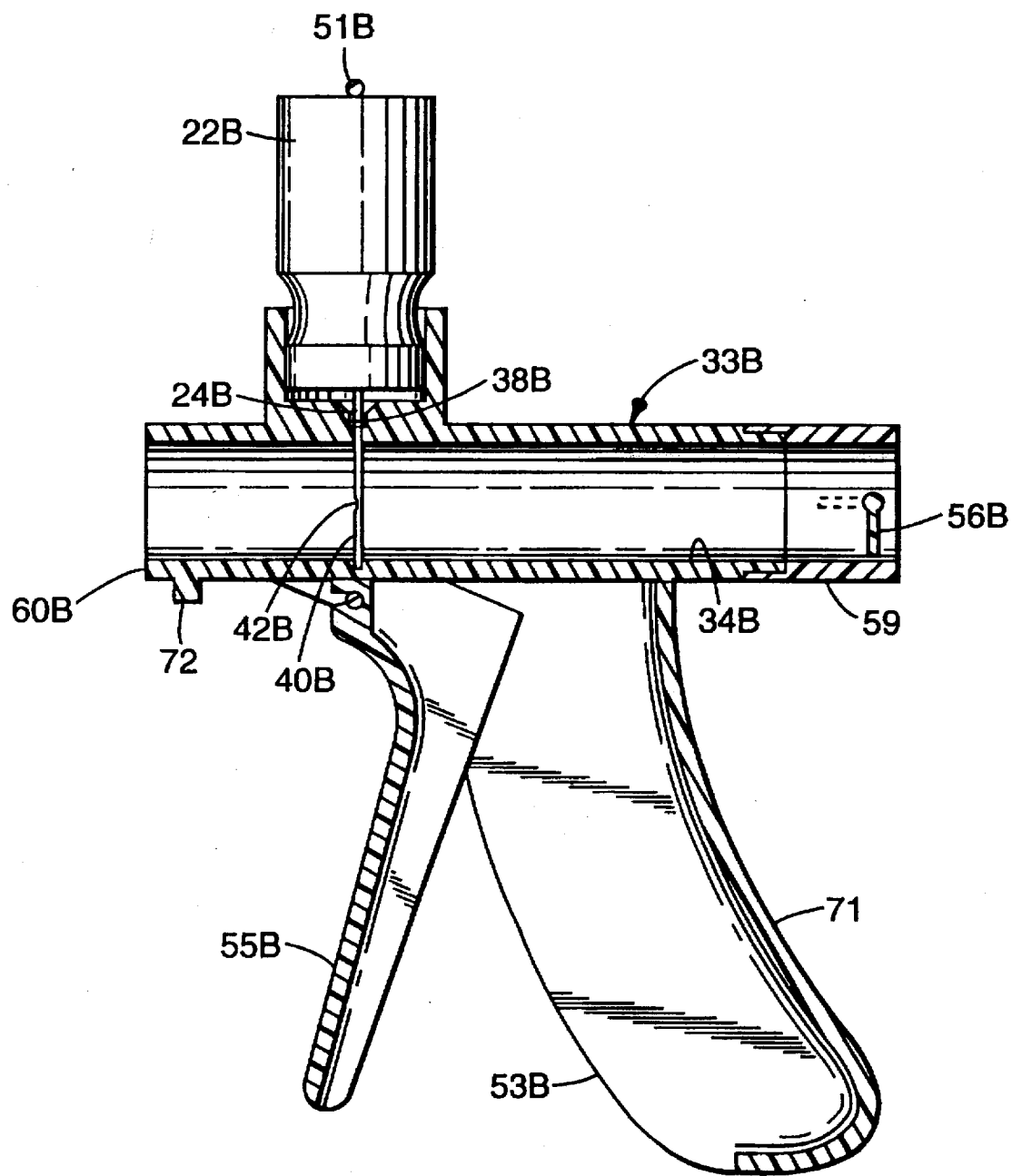
FIG. 11 is a sectional view of portions of an aerosol generating device that is slightly different than the aerosol generating device of FIG. 10 and which shows an optional orienting mechanism.
Figure 12:
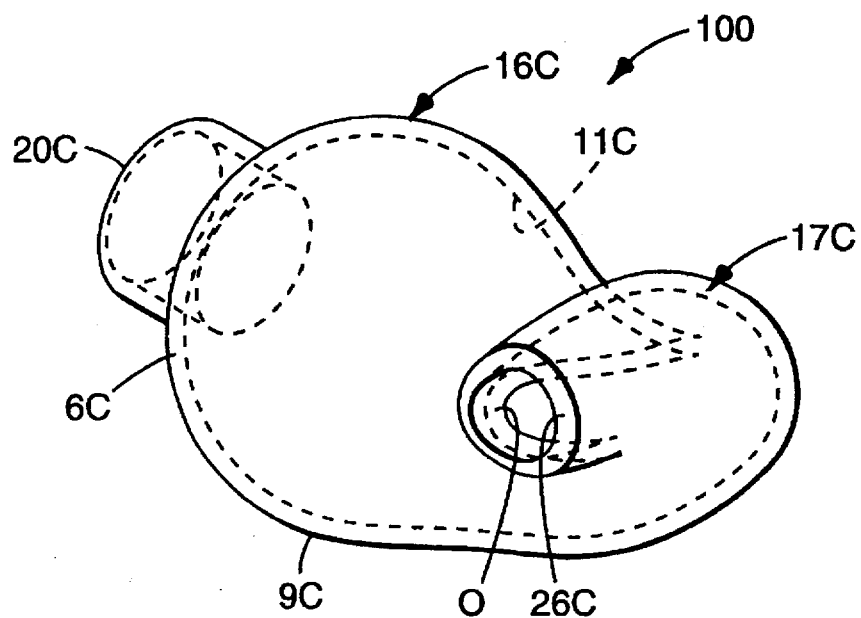
FIG. 12 is a perspective view of another embodiment of conduit according to the present invention.
Figure 13:
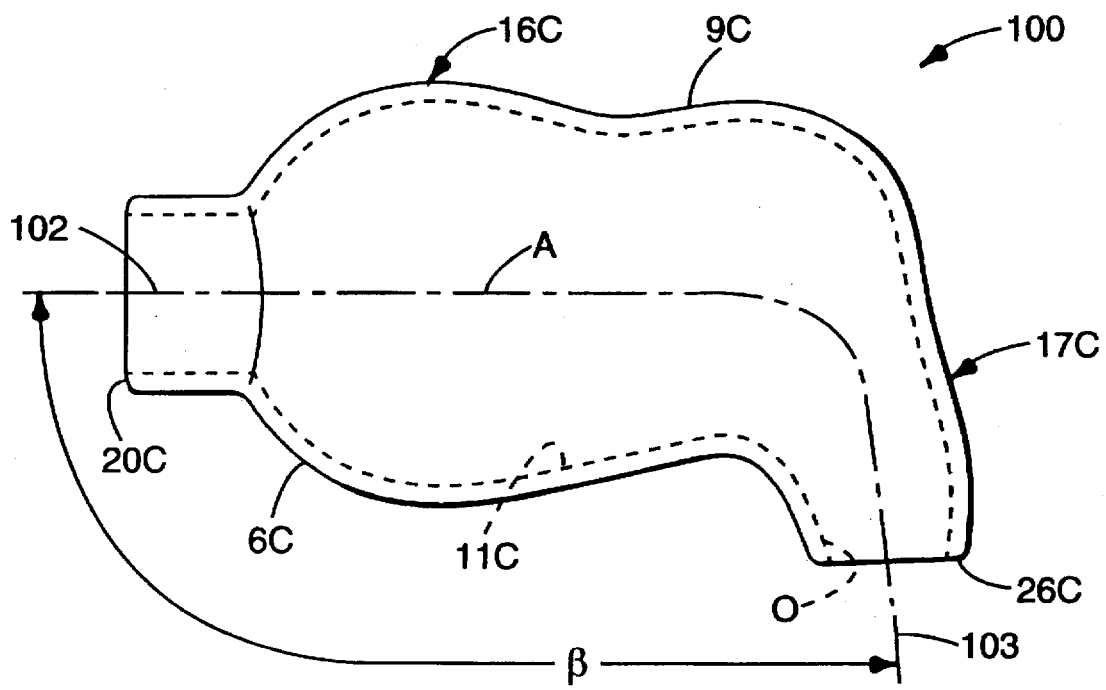
FIG. 13 is a top view of the conduit of FIG. 12.
Figure 14:
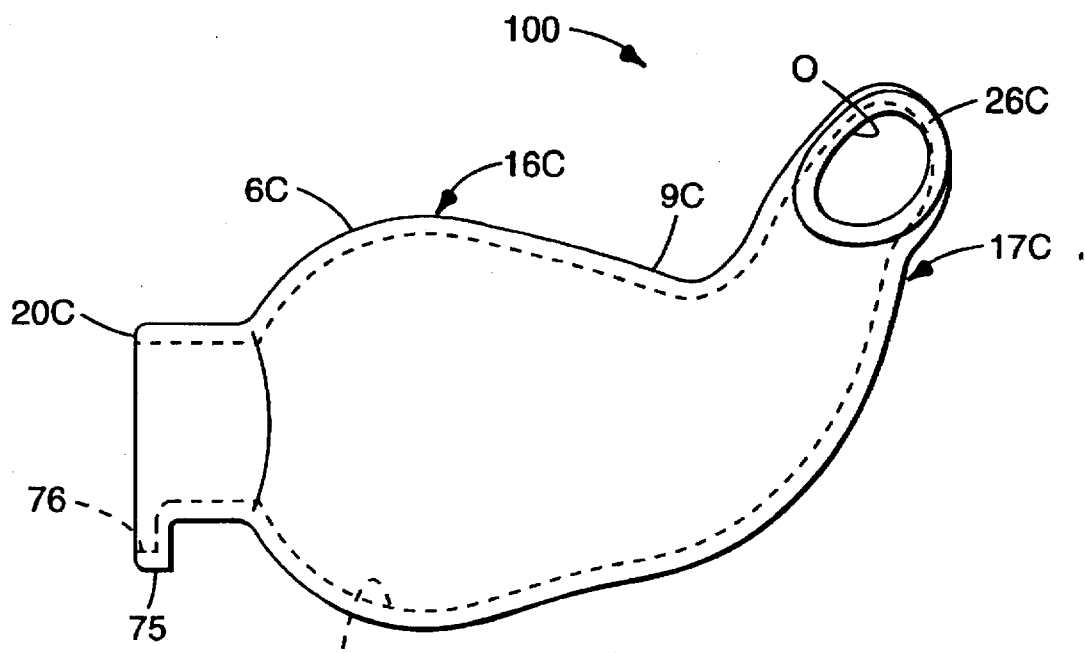
FIG. 14 is a side view of the conduit of FIG. 12, with the exception that an optional finger rest with groove for use with the orienting mechanism of FIG. 11 has been added.
Figure 15:
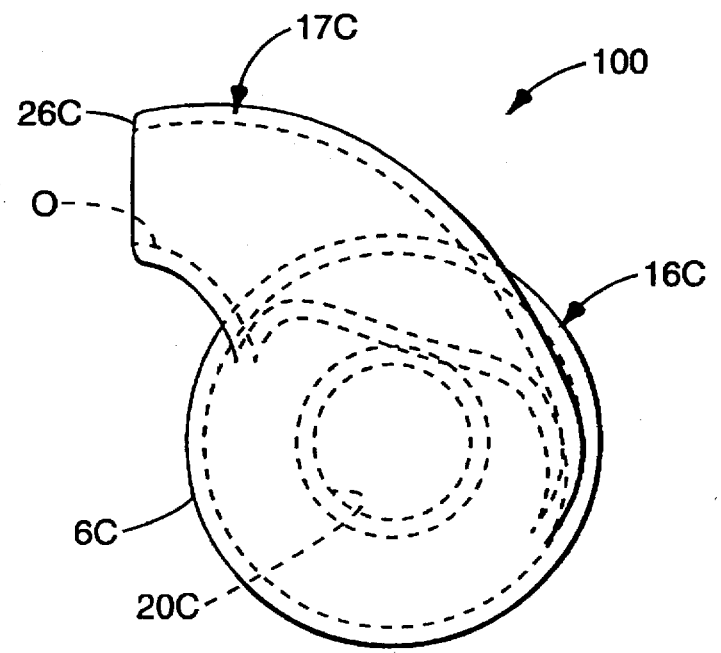
FIG. 15 is a distal end view of the conduit of FIG. 12.

The proximal end 20 of the conduit 10 may be attached to the body 33 by any suitable manner. Preferably, while the body 33 should be firmly attached to the conduit 10, the body 33 should readily separate from the conduit 10 in the event that an animal suddenly violently shakes or moves its head. For example as shown in FIG. 3, the conduit 10 is constructed from a resilient, flexible material which affords stretching the distal end 20 over an end 60 of the body 33 to form a tight friction fit. Optionally, a radial clamp may be used to enhance this friction fit. The mounting assembly shown in FIG. 3 constitutes one illustrative design of a tube-connecting means, although other types of connections are also contemplated.

In use, the air openings 36 and air passageway 34 are preferably in fluid communication with the lumen of the distal end 20 of the conduit 10. As a result, air is permitted to flow freely through the air opening 36 of the aerosol-dispensing device 18. During inhalation through the conduit 10, air travels inwardly from the air (inlet) opening 36 through the air passageway 34 and lumen of the first section 16 which functions as an expansion chamber to afford expansion of the dose of aerosolized medicament. From the lumen of the first section 16, the aerosol (e.g. aerosolized medicament) flows into the lumen of the second section 17 and then through the respiratory passages 1 of the horse 14 and ultimately to its lungs (if a respirable aerosol is sought to be delivered).

FIGS. 9 and 10 illustrate another embodiment of a body for associating the conduit (e.g. 10) with a canister (e.g. 22A), generally designated by reference character 33A. The body 33A includes many features similar to the body 33 which are identified by the same reference number to which the suffix "A" has been added.

Like the body 33 and canister 22, the body 33A and canister 22A include a hollow stem 24A, a stem receptacle 38A, a hollow tube 40A with orifice 42A, and an end 60A adapted to be connected to the conduit 10. The body 33A includes a trigger 55 movable relative to the rest of the body 33A between cocked and fired positions. The canister 22A is slip or friction fit to the body 33A. Bail 51 also assists in coupling the canister 22A to the body 33A.

The bail 51 is operatively connected to the trigger 55 and moves the canister 22A relative to the stem 40A when the trigger 55 is manually moved from the cocked toward the fired position so that the trigger 55 actuates the stem 24A. The spring within the canister 22A returns the trigger 55 from the fired to the cocked position after the canister 22A is actuated.

Unlike the body 33, the body 33A includes a handle 53 which affords a pistol-like grip. When the conduit 10 is coupled to the body 33A, the pistol-like grip provided by the handle 53 affords ease of insertion of the distal end portion of the conduit 10 into the nostril of the animal, as the manipulations of the handle 53 which are required when inserting the conduit 10 are believed to be well within the average user's range of motion (e.g. wrist, hand and arm movements). Additionally, the handle 53 allows the user to firmly hold the body 33A and control the conduit 10 when the trigger 55 is squeezed.

Also unlike body 33, a proximal end portion of the air passageway 34A of the body 33A is situated at generally a right angle relative to the distal end portion of the air passageway 34A. This configuration of the air passageway 34A restricts the chance that an object (e.g. a user's hand) will restrict the passage of inspirator airflow through passageway 34.

The airflow indicator for the body 33A comprises an elastomeric balloon member 58 in fluid communication with the air passageway 34A. As the animal inhales through air passageway 34A, the pressure within air passageway 34A drops which causes the balloon 58 to collapse. Optimally, a user will actuate the trigger 55 when the balloon is collapsed.

FIG. 11 illustrates another embodiment of a body for associating the conduit (preferably conduit 100 described below) with a canister (e.g. 22B), generally designated by reference character 33B. The body 33B includes many features similar to the body 33 which are identified by the same reference number to which the suffix "B" has been added.

Like the body 33 and canister 22, the body 33B and canister 22B include a hollow stem 24B, a stem receptacle 38B, a hollow tube 40B with orifice 42B, an air passageway 34B, and an end 60B adapted to be connected to the conduit. As an example not intended to be limiting, the air passageway 34B may have a diameter of about 0.67 inches, a wall thickness of about 0.2 inches and an overall length of about 4.5 inches. The handle 53B may have a height of about 3.6 inches (measured from the bottom to the walls of the air passageway 34B) and a width of about one inch.

The handle 53B includes rear curved surfaces 71 that are adapted to approximate the surfaces of a user's palm just below the thumb. Those palm surfaces directly abut the surfaces 71 when the body 33A is grasped in a pistol-like fashion. As described in greater detail below, the body 33B optionally includes an orienting means 72 generally adjacent end 60B for use with an optional finger rest.

Like the body 33A, the body 33B includes a trigger 55B movable relative to the rest of the body 33B between cocked and fired positions. Bail 51B is operatively connected to the trigger 55B and moves the canister 22B relative to the stem 40A when the trigger 55B is moved from the cocked toward the fired position.

Unlike the body 33, the body 33B includes a vane 56B situated within a visibly transparent cylindrical housing 59. The vane 56B is adapted to deflect (e.g. FIG. 11 dashed lines) in response to airflow through the passageway 34B (FIG. 11, dotted lines) to indicate that inspiratory airflow is traveling through the passageway 34B.

FIGS. 12 through 17 illustrate a second, preferred embodiment of conduit according to the present invention generally designated by the reference character 100. The conduit 100 has features similar to the conduit 10 which are identified by the same reference character to which the reference character "C" has been added.

Like the conduit 10, the conduit 100 includes a generally bulbous-shaped first section 16C, a second section 17C, proximal 20C and distal 26C ends, an outlet O, sealing surfaces 6C, inner surfaces 11C defining a lumen and outer surfaces 9C.

The shape of the conduit 100 is slightly different than the shape of the conduit 10. The outer surfaces 9C are irregular shaped and are adapted to generally conform to the irregular shaped surfaces of the horse's nasal passageway.

Figure 16:
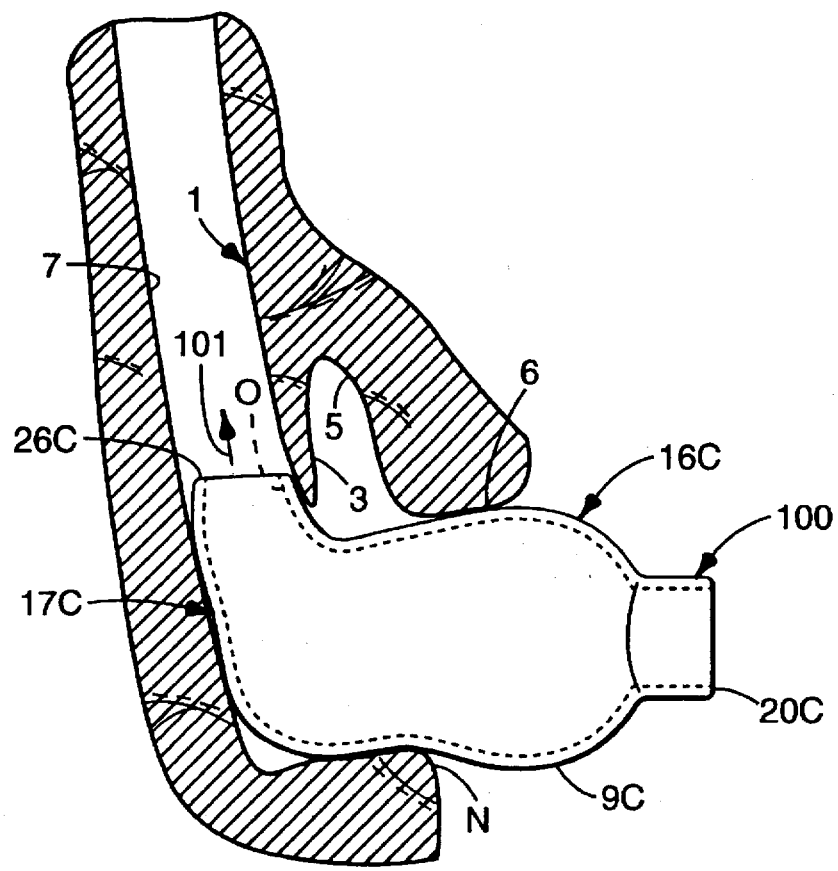
FIG. 16 is a partial sectional, schematic top view of the conduit of FIG. 13 schematically illustrating the position of the conduit within the nostril of a horse.
Figure 17:
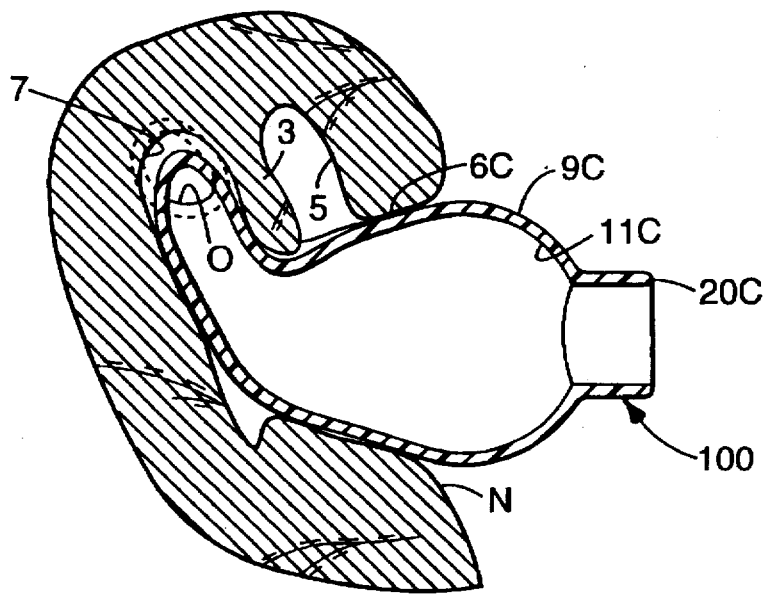
FIG. 17 is a partial sectional, schematic side view of the nostril and conduit of FIG. 16.

FIGS. 16 and 17 schematically illustrate how the outer surfaces 9C conform to the irregular shaped surfaces of the horse's nasal passageway after it has been inserted within the nasal passageway (e.g. into the nostril). The outlet O efficiently bypasses the alar fold 3 and preferably rests in the same position as that position of the conduit 10 described above with reference to FIG. 7.

Much of the outer surfaces 9C abut the tissue of the nasal passageway 1. Again, the conduit 100 has a sufficient length such that the orifice O does not allow passage of the aerosol into the nasal diverticulum 5 of the horse 14.

The lumen of the conduit 100 defines a central axis A (FIG. 13) extending from generally adjacent the connecting surfaces to the outlet O. The portion of the axis A generally adjacent the connecting surfaces (102 in FIG. 13) is situated at an angle Beta (B) of between about 0 and about 180 degrees (and most preferably about ninety degrees) relative to the portion of the axis generally adjacent the outlet O (103 in FIG. 13).

With the sealing surfaces 6C abutting the nostril N, the conduit 100 directs substantially all of that nostril's inspiratory airflow through the lumen 11C. Also, the conduit 100 affords passage of an aerosol in generally the same direction as the inspiratory airflow through the nostril. Such action is believed to beneficially entrain the aerosol in the inspiration airstream, and is particularly desirable when a respirable aerosol is to be delivered.

The inspiratory airflow through the nasal passageway 1 at the location of the outlet O defines a first direction 101 (FIG. 16). The conduit 100 affords passage of the aerosol through the outlet O in a direction that is generally parallel to the first direction to allow the aerosol to be beneficially entrained in the inspiration airstream.

Since the outer surfaces 9C of the conduit 100 generally conform to the irregular shaped surfaces of the horse's nasal passageway 1, the outer surfaces 9C tend to facilitate proper orientation of the conduit 100 within the nasal passageway 1. It is believed that a user will be readily able to discern whether the conduit 100 is properly oriented within the nostril due to the "feel" of the conduit 100 when it is within the nasal passageway 1.

To further facilitate proper orientation of the conduit 100 and ease of administration of the aerosol, the conduit 100 may optionally include a finger rest 75 (FIG. 14) which includes a groove 76 adapted to receive the orienting means 72 described above in conjunction with the body 33B (FIG. 11). When the proximal end 20C of the conduit 100 is connected to the body 33B, the orienting means 72 is received within the groove 76 to ensure that the body 33B (including the handle 53B) is properly oriented relative to the conduit 100. A user's finger may be placed on the finger rest to augment the user's control of the conduit 100 as it is being inserted into the nostril.

As an example not intended to be limiting, the first section 16C of the nasal conduit 100 may have a maximum outer diameter of approximately 2⅜ inches, the second section 17 may have an outer diameter at the outlet O of approximately ⅞ inches, and the conduit 100 may have a generally constant overall thickness of about ⅛ inches. The generally cylindrical portion of the conduit 100 generally adjacent the proximal end 20C has an outlet diameter of about 0.85 inches tapering to 0.78 inches just prior to opening into the expansion chamber. The conduit 100 has a length as measured horizontally from the extreme left to the extreme right in FIG. 14 of about 4⅝ inches, and a height as measured vertically from the extreme top to the extreme bottom in FIG. 14 of about 3⅛ inches.

The bodies 33, 33A and 33B may be constructed from any suitable material, and preferably a material suitable for medical purposes. Examples include metals and plastics. If an aerosol medicament is dispensed from the canister, the material should be compatible with the medicament.

The conduits 10 and 100 are preferably constructed from a flexible, resilient material. The material should be sufficiently flexible to generally conform to the inner surfaces of the horse's nasal cavity, such as the nasal cartilage and nasal mucosa, to restrict irritation of sensitive tissue. Also, the material should be sufficiently resilient to avoid or restrict collapse when a portion of the conduit (e.g. 100) is placed in the nasal passageway of the horse so that the outlet O remains in fluid communication with the aerosol generating device 18. Materials that may be used to construct the conduit include but are not limited to elastomers (e.g. rubber-like material), plastics and plastic-like materials. Particular examples include polyethylene (e.g. an FDA approved LDPE or EVA Copolymer polyethylene), a silastic, a flexible polyvinylchloride, or a flexible polyester. The conduits may be constructed using any suitable procedures, such as injection molding, dip molding, spin molding, and blow molding. The conduits 10 and 100 may be constructed using the techniques described in Example 1 below.

The conduit 100 may be used with an aerosol generating device comprising the body 33B and canister 22B in a method of administering a respirable aerosol to a large animal, also according to the present invention. The method comprises the steps of (1) providing an aerosol generating device (e.g. 18), (2) providing a conduit (e.g. 10 or 100), (3) connecting the conduit to the aerosol generating device so that the outlet O of the conduit is in fluid communication with the aerosol generating device, (4) inserting the distal end of the conduit into the nostril of the large animal; and (5) then actuating the aerosol generating device to deliver the respirable aerosol.

TEST RESULTS

A series of tests were performed on several different sizes and shapes of conduits to determine their aerosol output or "throughput". The first shapes of nasal conduits that were tested were three hydrometer bulbs or "eyedropper" conduits. A small, medium and large "eyedropper" shape were tested. A hole was cut in the large end of each of the eyedroppers. The small, medium and large bulbs had lengths, maximum outer diameters and outlet opening diameters of 2¹/₁₆, 2¹³/₁₆, 3¼; 1¹³/₁₆, 2⅜, 2⁹/₁₆; ½, ½, ⅝ inches respectively. The small conduit had a volume of about forty-one (41) milliliters, the medium approximately ninety-five (95) milliliters, and the large about one-hundred-twenty (120) milliliters.

A second conduit configuration was generally spherical (69 ml) and had an overall length of about 2⅝ inches, an orifice outlet diameter of about ¹¹/₁₆ inches, a maximum outer diameter of about 2³/₁₆ inches, and a volume of about sixty-nine (69) milliliters.

An aerosol generating device similar to the device shown in FIG. 1–3 was utilized. The aerosol generating device utilized a Maxair™ canister with a 50 microliter valve. Four actuations of 200 micrograms delivery per actuation were utilized. Airflow at 50 LPM was drawn through the actuator-conduit with four actuations of the aerosol canister occurring during each test. A total of three tests were performed for each configuration of the conduits and the results were based on the average of these three tests.

Figure 8:
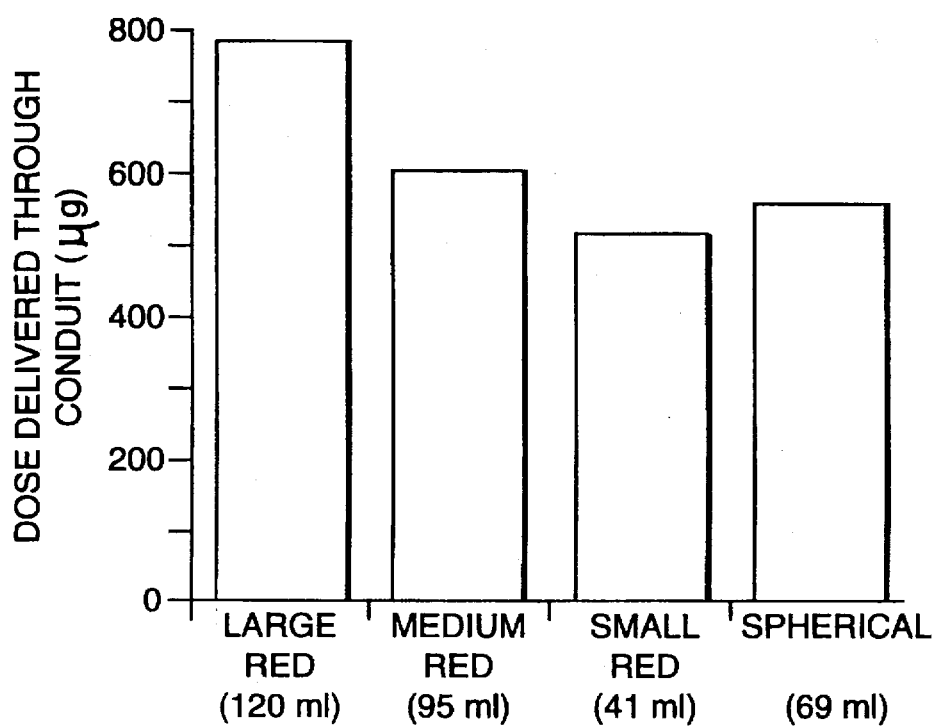
FIG. 8 illustrates test results for several different experimental conduits.
Figure 9:
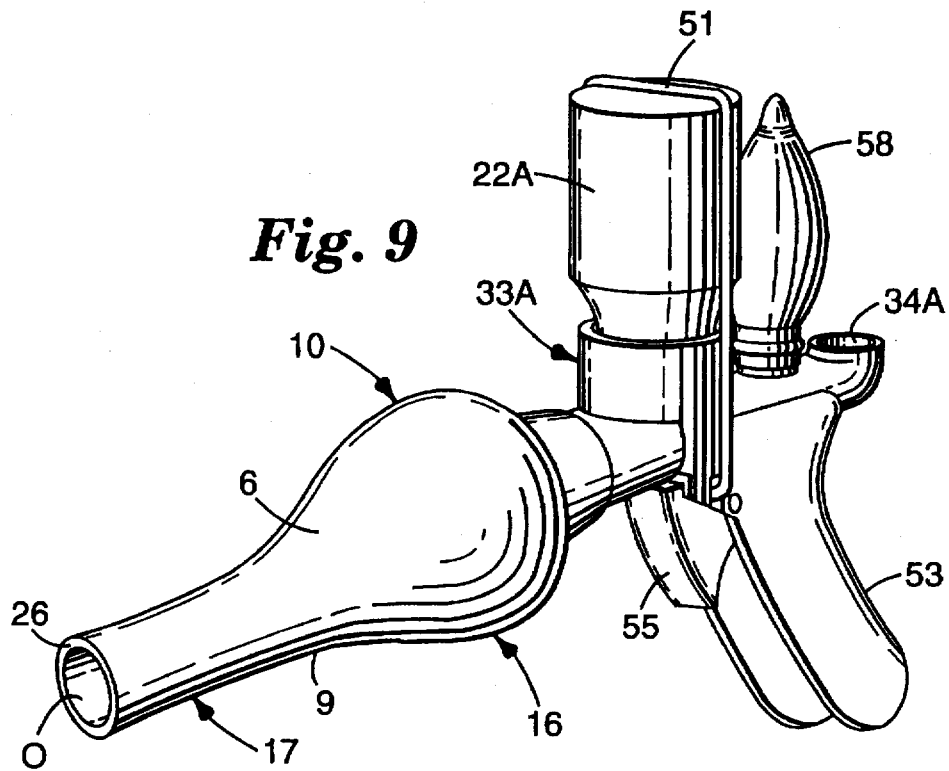
FIG. 9 is a perspective view of the conduit of FIG. 5 attached to an aerosol generating device different than the aerosol generating device shown in FIGS. 3 and 4.
Figure 10:
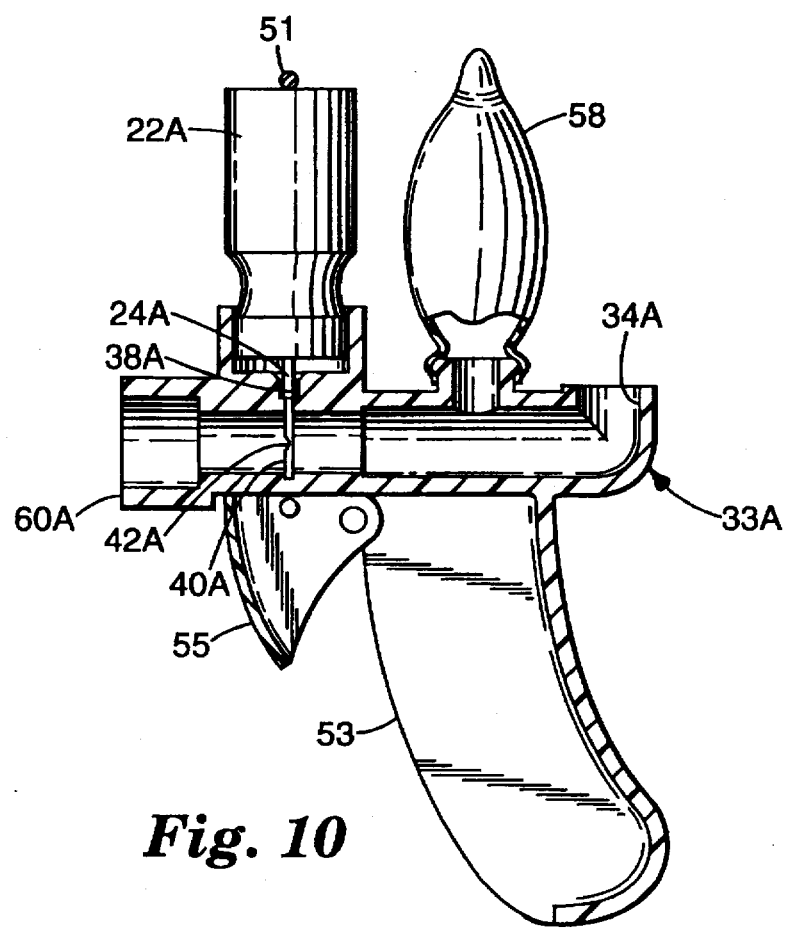
FIG. 10 is a partial sectional view of the aerosol generating device of FIG. 9 illustrating one embodiment of an airflow indicator.

FIG. 8 is a bar graph illustration of the results of these tests. The large conduit allowed 98% of the predicted aerosol output to pass through. As conduit size decreased, aerosol output likewise decreased (medium 76% and small 65%). The spherical shaped nasal conduit allowed 71% of the predicted output to pass through.

The four nasal conduits mentioned above were coupled to an aerosol generating device (similar to reference character 18 shown in FIGS. 2 and 3) and were tested on live horses. It was found that the large and small nasal conduits did not have a preferential fit with the anatomy of the external nostril. The spherical nasal conduit had the least desirable fit as it did not form a preferred seal with the surfaces surrounding the nostril of the animal. The medium sized nasal conduit was the most preferred as it fit the external nostril of both ponies and horses.

A second test on the medium nasal conduit was performed to test its ability to deliver an experimental, investigational dose of a bronchodilator (e.g. a dose of 3200 micrograms of the pirbuterol acetate bronchodilator, sold under the name Maxair™ Inhaler generally available from 3M Pharmaceuticals of St. Paul, Minn.).

A pony with sufficiently compromised airways due to COPD (chronic obstructive pulmonary disease) was instrumented for measuring airway mechanics. The pulmonary function of the pony was tested both before and after the administration of a drug according to the following method (See F. J. Derksen et al., Aerosol Pirbuterol: Bronchodilator Activity and Side Effects in Ponies with Recurrent Airway Obstruction (Heaves), Equine Veterinary Journal 24(2): 107–112 (1992); and F. J. Derksen et al., Pulmonary Function in Standing Ponies: Reproducibility and Effect of Vagal Blockade, Am. J. Vet Res. 43, 598–602 (1982) the entire contents of each incorporated by reference).

An esophageal balloon, attached to a catheter is placed into the distal third of the esophagus and connected to a calibrated pressure transducer (Validyne Model DP45-34 generally available from Validyne, of Northridge, Calif.). The position of the esophageal balloon is adjusted to obtain the maximum change in pleural pressure during tidal breathing. A #5 Fleisch pneumotachograph (available from Gould, Inc. of Minneapolis, Minn.) is mounted on a face mask which covers the external nares. The face mask is taped to the face to prevent leaks. The Fleisch pneumotachograph is connected to a pressure transducer (Validyne Model DP43-22) that provides a signal proportional to airflow. The flow signal passes to a Buxco pulmonary function computer (available from Buxco Electronics, Inc., of Sharon, Conn.) that integrates the signal to provide tidal volume. Flow, tidal volume and transpulmonary pressure ($\Delta P_{pl}$) during breathing are processed by the lung function computer to provide a breath-by-breath measurement of pulmonary resistance ($R_L$) and dynamic compliance ($C_{dyn}$). Thirty breaths are used to calculate ($\Delta P_{pl}$), ($R_L$) and ($C_{dyn}$) at each observation time point. Pulmonary function measurements are made prior to administration of the aerosols to qualify the pony for testing and to obtain baseline values.

Table 1 illustrates the results obtained from testing the medium sized nasal conduit. Within nine to ten minutes after administration of the medicament, significant bronchodilation of the airways had occurred. The results indicate that the aerosol dosage or bolus effectively traverses the labyrinth of the nasal cavity in sufficient quantity to reach the active sites within the lung to induce bronchodilation.

TABLE 1

Pulmonary Function Tests of COPD Pony Treated With 3200 µg Pirbuterol Acetate Using Actuator-Conduit System**
(Mean values during each time period)

| Time | MAX $\Delta P_{pl}$ | $R_L$ | $C_{dyn}$ |
|---|---|---|---|
| Pre-Treatment | 37.1 | 5.47 | 0.119 |
| Post-Treatment | | | |
| 0:49–1:45 | 17.4 | 1.40 | 0.929 |
| 1:55–2:37 | 9.2 | 1.31 | 0.738 |
| 2:52–3:53 | 11.5 | 1.37 | 0.665 |
| 3:55–4:57 | 20.6 | 1.46 | 1.308 |
| 4:59–5:57 | 13.4 | 1.27 | 1.524 |
| 5:59–6:24 | 13.2 | 1.23 | 2.233 |
| 7:11–7:47 | 10.6 | 0.94 | 2.381 |
| 8:05–8:49 | 11.6 | 1.14 | 4.835 |
| 8:50–9:18 | 11.8 | 0.90 | 3.193 |
| Post-TX Mean | 13.3 | 1.22 | 1.978 |
| Percent Change from Pre-Tx mean | 64.0% (decrease) | 77.7% (decrease) | 1,562% (increase) |

$\Delta P_{pl}$ = general pressure measurement (pulmonary pressure)
$R_L$ = resistance in cm H2O/L/sec
$C_{dyn}$ = dynamic compliance in L/cm H2O
**16 actuations of Metered Dose Inhaler canister @ 200 μg pirbuterol/actuation Visual confirmation that an aerosolized medicament dose actually reached the horse's lung was accomplished through bronchoscopy. A fiberoptic bronchoscope was inserted into the trachea of the horse with its tip residing just above the carina. The distal end of the medium sized nasal conduit was then placed in the external nostril of the horse and the canister actuated concurrent with the horse's inspiratory effort. The aerosol cloud was clearly seen to enter both the bronchi of the horse lung. This is evidence that the resultant bronchodilation recorded in Table 1 was in fact due to medicament acting directly on the airways.

EXAMPLE 1

To develop a preferred shape of the nasal conduit (e.g. an anatomically correct shape, 100), a cast of the external nostril and a portion of the internal nasal passageway was initially constructed. To construct the cast, a vinyl polysiloxane (Express™ brand dental registration and impression material, No. 7312, generally available from the Minnesota Mining and Manufacturing Company of St. Paul, Minn. (3M)) was formed into a six (6) to eight (8) inch tube and was then pressed into the left nasal passageway of a live horse. The material was left in place to harden (approximately six minutes) and then it was removed. The space of the nasal diverticulum was manually removed from the hardened material. The resultant, hardened material represented a negative image of the internal equine nostril except for the nasal diverticulum.

The same impression material was also formed into a flat sheet that was placed over the external nare of the horse using only the force required to form the material over the external anatomy of the horse nare. This second, hardened material represented a negative impression of the external anatomy of the horse nare.

The impression of the external nare anatomy (the second hardened material) was then placed on the surface of freshly prepared patching plaster (Bondex), anatomy side up, and carefully pressed into the plaster. The plaster was allowed to set and was used as a base for forming the cast.

The impression of the internal nare was then glued to the external nare impression. A tube was then placed over both impressions and filled with liquid silastic (generally available from Dow Corning). The silastic was then allowed to cure for several days until hard. The Express™ casts were then removed from the silastic leaving behind a positive image of the equine nostril and external nare.

This cast was then used to generate the solid form of the equine nasal conduit. Again Express™ (No. 7301H) was injected into the nasal cavity of the cast just beyond the juncture to the diverticulum. The injection process continued backwards toward the opening of the nare until it was just even with the fold for the nasal septum. The tip of a rubber laberatory hydrometer bulb similar to the medium sized bulb described in the test results was cut off such that the opening (internal diameter) coincided with the opening to the external nare of the mold. The opposite end of the bulb has a small hole cut into it so that Express™ could be injected via that port. The bulb was carefully placed onto the Express™ previously injected into the mold and then filled with additional Express™. This was allowed to harden. Once set, the bulb was removed and the entire Express™ casting was removed from the positive mold resulting in a solid bulb-like conduit that had a tapered tip shaped to conform to the internal anatomy of the equine nostril and to the nare.

This solid bulb was laser scanned to generate an electronic three dimensional model using a conventional laser scanner. The electronic data was used to create a three dimensional computer model of the conduit using Unigraphics CAD (Computer Assisted Design) software. The CAD file of the computer model was used as the input data source for a Cubital Rapid Prototyping System (available from Cubital America Inc., of Warren, Mich.) to create a master model. The master model was placed in a frame. The frame was filled with an RTV silicone polymer which was subsequently cured to provide a silicone mold. The silicone mold was injected with a polyurethane polymer (REN-RP6401 polyurethane, generally available from Ceiba-Geigy of Fast Lansing, Mich.) and then spun along various axes to distribute the urethane over the inner surface of the mold (rotational molding). After the urethane had set, the halves of the mold were separated to provide a hollow cast of the equine nasal conduit 100.

The present invention has now been described with reference to several embodiments thereof. It will be apparent to those skilled in the art that many changes or additions can be made in the embodiments described without departing from the scope of the present invention. For example, a suitable alternative apparatus may comprise a hollow tube 40 with an orifice 42 located generally adjacent the distal end 26 of the conduit 10 in the manner shown in coassigned U.S. Pat. No. 5,231,983. Thus, the scope of the present invention should not be limited to the structure described in this application, but only by structures described by the language of the claims and the equivalents of those structures.

What is claimed is:

1. Apparatus adapted to be at least partially inserted into a nostril of a large animal such as a horse for administering an aerosol to the large animal, the large animal having a nasal passageway and a nasal-pharyngeal cavity, the apparatus being adapted for use with an aerosol generating device, the apparatus comprising:

a conduit having outer surfaces, a proximal end, a distal end having an outlet, and inner surfaces that are sized and shaped to afford passage of an aerosol through the conduit, the inner surfaces defining a lumen extending between the proximal and distal ends and opening to said outer surfaces at said outlet, the lumen being sized and shaped to afford expansion of an aerosol during at least a portion of the passage through the conduit;

the conduit having a length which affords locating the outlet in the nasal passageway of the large animal without projecting into the nasal-pharyngeal cavity of the large animal; and connecting surfaces for connecting the conduit to an aerosol generating device so that the outlet of the conduit may be placed in fluid communication with an aerosol generating device.

2. An apparatus according to claim 1 wherein the conduit affords passage of aerosol in generally the same direction as the inspiratory airflow through the nostril.

3. An apparatus according to claim 1 wherein the lumen has a central axis extending from the connecting surfaces to the outlet, and the portion of the axis generally adjacent the connecting surfaces is situated at approximately a right angle with respect to the portion of the axis generally adjacent the outlet.

4. An apparatus according to claim 1 wherein the outer surfaces are irregular shaped to conform to the irregular shaped surfaces of the large animal's nasal passageway.

5. Apparatus adapted to be at least partially inserted into a nostril of a large animal for administering an aerosol to the large animal, the large animal having a nasal passageway, a nasal diverticulum, and a nasal-pharyngeal cavity, the apparatus being adapted for use with an aerosol generating device, the apparatus comprising:

a conduit having outer surfaces, a proximal end, a distal end having an outlet, and inner surfaces that are sized and shaped to afford passage of an aerosol through the conduit, the inner surfaces defining a lumen extending between the proximal and distal ends and opening to said outer surfaces at said outlet, the lumen being sized and shaped to afford expansion of an aerosol during at least a portion of the passage through the conduit;

the conduit having a length which affords locating the outlet in the nasal passageway of the large animal without projecting into the nasal-pharyngeal cavity of the large animal;

connecting surfaces for connecting the conduit to an aerosol generating device so that the outlet of the conduit may be placed in fluid communication with an aerosol generating device, and when the conduit is fully inserted into the nostril of the large animal, the conduit is sized and shaped and has a sufficient length to avoid situating the outlet such that it opens in a position that allows passage of the aerosol into the nasal diverticulum of the large animal.

6. Apparatus adapted to be at least partially inserted into a nostril of a large animal for administering an aerosol to the large animal, the large animal having a nasal passageway and a nasal-pharyngeal cavity, the apparatus being adapted for use with an aerosol generating device, the apparatus comprising:

a conduit having outer surfaces, a proximal end, a distal end having an outlet, and inner surfaces affording passage of an aerosol through the conduit, the inner surfaces defining a lumen extending between the proximal and distal ends and opening to said outer surfaces at said outlet, the lumen being sized and shaped to afford expansion of an aerosol during at least a portion of the passage through the conduit;

the conduit having a length which affords locating the outlet in the nasal passageway of the large animal without projecting into the nasal-pharyngeal cavity of the large animal;

connecting surfaces for connecting the conduit to an aerosol generating device so that the outlet of the conduit may be placed in fluid communication with an aerosol generating device, the conduit has first and second sections, with the outlet situated in the second section and with the connecting surfaces situated in the first section, the first and second sections of said conduit having cross-sections, the cross-sectional area of a cross-section in the first section is generally larger than the cross-sectional area of a cross-section in the second section so that inner surfaces of the first section of the conduit form an expansion chamber to afford expansion of the aerosol, and wherein the first section is generally bulbous shaped.

7. Apparatus adapted to be at least partially inserted into a nostril of a large animal such as a horse for administering an aerosol to the large animal, the large animal having a nasal passageway and a nasal-pharyngeal cavity, the apparatus being adapted for use with an aerosol generating device, the apparatus comprising:

a conduit having outer surfaces, a proximal end, a distal end having an outlet, and inner surfaces affording passage of an aerosol through the conduit, the inner surfaces defining a lumen extending between the proximal and distal ends and opening to said outer surfaces at said outlet, the lumen being sized and shaped to afford expansion of an aerosol during at least a portion of the passage through the conduit;

the conduit having a length which affords locating the outlet in the nasal passageway of the large animal without projecting into the nasal-pharyngeal cavity of the large animal;

connecting surfaces for connecting the conduit to an aerosol generating device so that the outlet of the conduit may be placed in fluid communication with an aerosol generating device, wherein said conduit is constructed from a flexible, resilient material adapted to generally conform to the large animal's nasal passageway, and to restrict collapse when a portion of the conduit is placed in the nasal passageway of the large animal so that the outlet remains in fluid communication with the aerosol generating device, and wherein when the conduit is fully inserted into the nostril of the large animal, the outlet is located in the large animal's nasal vestibule and is bounded medially by the nasal septum, dorso-laterally by the alar fold and ventrally by nasal mucosa.

8. An apparatus adapted to be at least partially inserted into a nostril of a large animal for administering a respirable aerosol having a component for delivery beyond the upper respiratory tract and to the peripheral lung field of the large animal, the component having an appreciable amount of medicament particles having a size of less than about thirty (30) micrometers, the large animal having a nasal passageway and a nasal-pharyngeal cavity, the apparatus being adapted for use with an aerosol generating device capable of providing a respirable aerosol, the apparatus comprising:

a conduit having outer surfaces, a proximal end, a distal end having an outlet, and inner surfaces affording passage of an aerosol through the conduit, the inner surfaces defining a lumen extending between the proximal and distal ends and opening to said outer surfaces at said outlet, the lumen being sized and shaped to afford expansion of an aerosol during at least a portion of the passage through the conduit so that a respirable aerosol may exit the outlet after passage through the conduit;

the conduit having a length which affords locating the outlet in the nasal passageway of the large animal without projecting into the nasal-pharyngeal cavity of the large animal;

connecting surfaces for connecting the conduit to an aerosol generating device so that the outlet of the conduit may be placed in fluid communication with an aerosol generating device.

9. Apparatus adapted to be at least partially inserted into a nostril of a large animal for administering an aerosol to the large animal, the large animal having a nasal passageway and a nasal-pharyngeal cavity, the apparatus being adapted for use with an aerosol generating device, the apparatus comprising:

a conduit having outer surfaces, a proximal end, a distal end having an outlet, and inner surfaces affording passage of an aerosol through the conduit, the inner surfaces defining a lumen extending between the proximal and distal ends and opening to said outer surfaces at said outlet, the lumen being sized and shaped to afford expansion of an aerosol during at least a portion of the passage through the conduit;

the conduit having a length which affords locating the outlet in the nasal passageway of the large animal without projecting into the nasal-pharyngeal cavity of the large animal;

connecting surfaces for connecting the conduit to an aerosol generating device so that the outlet of the conduit may be placed in fluid communication with an aerosol generating device, an inlet substantially adjacent the proximal end of the conduit, which inlet is sized and shaped to afford entry of inspiratory airflow through the conduit, the inspiratory airflow passing through the conduit and exiting the outlet; and said outer surfaces of said conduit comprise sealing surfaces adapted to abut the tissue surrounding the nostril of the large animal so that substantially all of the inspiratory airflow through that nostril flows through the lumen of the conduit.

10. Apparatus adapted to be at least partially inserted into a nostril of a large animal for administering an aerosol to the large animal, the large animal having a nasal passageway and a nasal-pharyngeal cavity, the apparatus being adapted for use with an aerosol generating device, the apparatus comprising:

a conduit having outer surfaces, a proximal end, an inlet, a distal end having an outlet, and inner surfaces affording passage of an aerosol through the conduit, the inner surfaces defining a lumen extending between the proximal and distal ends and opening to said outer surfaces at said outlet, the lumen being sized and shaped to afford expansion of an aerosol during at least a portion of the passage through the conduit;

the conduit having a length which affords locating the outlet in the nasal passageway of the large animal without projecting into the nasal-pharyngeal cavity of the large animal;

connecting surfaces for connecting the conduit to an aerosol generating device so that the outlet of the conduit may be placed in fluid communication with an aerosol generating device, wherein the outer surfaces include sealing surfaces for abutting the nostril of the large animal so that substantially all of the inspiratory air flow through that nostril flows in the inlet, through the lumen and out the outlet of the conduit, and when the conduit is fully inserted into the nostril of the large animal, the inspiratory airflow through the large animal's nasal passageway at the location of the outlet defines a first direction, and the conduit affords passage of the aerosol through the outlet in a direction that is generally parallel to the first direction.

11. In combination, an apparatus adapted to be at least partially inserted into a nostril of a large animal for administering an aerosol to the large animal, the large animal having a nasal passageway and a nasal-pharyngeal cavity, and an aerosol generating device, the apparatus comprising:

a conduit having outer surfaces, a proximal end, a distal end having an outlet, and inner surfaces that are sized and shaped to afford passage of an aerosol generated by the aerosol generating device through the conduit, the inner surfaces defining a lumen extending between the proximal and distal ends and opening to said outer surfaces at said outlet, the lumen being sized and shaped to afford expansion of an aerosol during at least a portion of the passage through the conduit;

the conduit having a length which affords locating the outlet in the nasal passageway of the large animal without projecting into the nasal-pharyngeal cavity of the large animal;

connecting surfaces for connecting the conduit to an aerosol generating device so that the outlet of the conduit may be placed in fluid communication with the aerosol generating device, the aerosol generating device comprises a canister of the type for dispensing a metered dose of aerosol medicament through a hollow stem when the stem is actuated, the connecting surfaces are connected to a means for associating the conduit with the canister comprising: a body having an air passageway adapted to be placed in fluid communication with the lumen of the conduit, and an air opening, the body including:

a stem receptacle generally adjacent the air passageway for receiving the stem of the canister, means for mounting the canister for movement relative to the stem to actuate the stem; and a hollow tube communicating with a hollow stem in the stem receptacle, the hollow tube having an outlet opening into the air passageway for delivering a metered aerosol dose to the air passageway for administration through the conduit to the large animal.

12. A combination according to claim 11 wherein the body includes a handle which affords a pistol-like grip, and a trigger movable between a cocked and fired position.

13. A combination according to claim 12 further including means for moving the canister relative to the stem when the trigger is moved from the cocked toward the fired position so that the trigger may actuate the stem.

14. A combination according to claim 11 wherein the body further comprises an air flow indicator.

15. A combination according to claim 14 wherein the indicator is mounted in the air passageway of the body and includes a vane movable in response to air flow through the lumen of the conduit and adapted to generate a visible, tactile or audible signal when moved.

16. A combination according to claim 11 wherein the body includes means for detachably attaching the canister to the body.

17. In combination, an aerosol generating device for generating a respirable aerosol for delivery to a large animal with a nasal-pharyngeal cavity and a nasal diverticulum, the respirable aerosol having a component for delivery beyond a large animal's upper respiratory tract and to the lungs of the large animal, and a conduit for administering the respirable aerosol to the large animal, the conduit comprising:

outer and inner surfaces, a proximal end, and a distal end having an outlet, the inner surfaces defining a lumen extending between the proximal and distal ends and opening to said outer surfaces at said outlet;

the conduit having a length which affords locating the outlet in the nasal passageway of the large animal without projecting into the nasal-pharyngeal cavity of the large animal;

means for connecting the conduit to the aerosol generating device so that the outlet of the conduit is in fluid communication with the aerosol generating device; and wherein when the conduit is fully inserted into the nostril of the large animal, the conduit is sized and shaped and has a sufficient length to avoid situating the outlet such that it opens in a position that allows passage of the aerosol into the nasal diverticulum of the large animal.

18. A combination according to claim 17 wherein the conduit has first and second sections, with the outlet situated in the second section and with the connecting surfaces situated in the first section.

19. A combination according to claim 18 wherein the first and second sections of said conduit have cross-sections, wherein the cross-sectional area of a cross-section in the first section is generally larger than the cross-sectional area of a cross-section in the second section so that inner surfaces of the first section of the conduit form an expansion chamber to afford expansion of the respirable aerosol.

20. A combination according to claim 19 wherein the first section is generally bulbous shaped.

21. A combination according to claim 17 wherein said conduit is constructed from a flexible, resilient material adapted to generally conform to the large animal's nasal passageway, and to restrict collapse when a portion of the conduit is placed in the nasal passageway of the large animal so that the outlet remains in fluid communication with the aerosol generating device.

22. A combination according to claim 17 wherein said outer surfaces of said conduit comprise:

sealing surfaces adapted to abut the tissue surrounding the nostril of the large animal so that substantially all of the inspiratory airflow through that nostril flows through the lumen of the conduit.

23. A combination according to claim 22 wherein: when the conduit is fully inserted into the nostril of the large animal, the inspiratory airflow through the nasal passageway at the location of the outlet defines a first direction, and the conduit affords passage of the respirable aerosol through the outlet in a direction that is generally parallel to the first direction.

24. A combination according to claim 17 wherein the lumen has a central axis extending from the connecting surfaces to the outlet, and the portion of the axis generally adjacent the connecting surfaces is situated at approximately a right angle with respect to the portion of the axis generally adjacent the outlet.

25. A combination according to claim 17 wherein the outer surfaces are irregular shaped to conform to the irregular shaped surfaces of the large animal's nasal passageway.

26. A combination according to claim 17 wherein the aerosol generating device comprises a canister of the type for dispensing a metered dose of a respirable aerosol medicament through a hollow stem when the stem is actuated, and the means for connecting the conduit to the aerosol generating device comprises:

a body having an air passageway adapted to be in fluid communication with the lumen of the conduit, and an air opening, the body including:

a stem receptacle generally adjacent the air passageway for receiving the stem of the canister, means for mounting the canister for movement relative to the stem to actuate the stem; and a hollow tube communicating with a hollow stem in the stem receptacle, the hollow tube having an outlet opening into the air passageway for delivering a metered aerosol dose to the air passageway for administration through the conduit to the large animal.

27. A combination according to claim 26 wherein the body includes a handle which affords a pistol-like grip, and a trigger movable between a cocked and fired position.

28. A combination according to claim 27 further including means for moving the canister relative to the stem when the trigger is moved from the cocked toward the fired position so that the trigger may actuate the stem.

29. A combination according to claim 26 wherein the body includes means for detachably attaching the canister to the body.

30. A combination according to claim 17 wherein the component is delivered to the large animal's peripheral lung field.

31. A combination according to claim 30 wherein the component has an appreciable amount of medicament particles having a size of less than about thirty (30) micrometers.

32. A combination according to claim 30 wherein the component has an appreciable amount of medicament particles having a size of less than about ten (10) micrometers.

33. A method of administering a respirable aerosol to a large animal such as a horse, the large animal having a nasal passageway and a nasal-pharyngeal cavity, the method comprising the steps of:

(1) providing an aerosol generating device capable of generating a respirable aerosol upon actuation;

(2) providing a conduit comprising: outer and inner surfaces, a proximal end, and a distal end having an outlet, the inner surfaces defining a lumen extending between the proximal and distal ends and opening to said outer surfaces at said outlet; the conduit having a length which affords locating the outlet in the nasal passageway of the large animal without projecting into the nasal-pharyngeal cavity of the large animal;

(3) connecting the conduit to the aerosol generating device so that the outlet of the conduit is in fluid communication with the aerosol generating device;

(4) inserting the distal end of the conduit into the nostril of the large animal; and (5) then actuating the aerosol generating device to deliver the respirable aerosol.

34. A method according to claim 33 wherein the step of providing a conduit comprises the step of providing outer surfaces which generally conform to the tissue of the large animals nasal passageway.

35. A method according to claim 33 wherein the step of inserting the distal end of the conduit into the nostril comprises the step of:

sealing the tissue surrounding the nostril of the large animal with sealing surfaces of the conduit so that substantially all of the inspiratory airflow through the nostril is directed through the lumen of the conduit.

36. A method according to claim 33 wherein the step of actuating the aerosol generating device to deliver the respirable aerosol comprises the steps of:

flowing inspiratory airflow through the nasal passageway at the location of the conduit outlet in a first direction, and directing passage of the respirable aerosol through the outlet in a direction that is generally parallel to the first direction.

37. A method of administering a respirable aerosol according to claim 33 wherein the step of providing an aerosol generating device capable of generating a respirable aerosol upon actuation comprises the step of:

providing an aerosol generating device capable of generating a respirable aerosol having a component for delivery beyond the upper respiratory tract and to the lungs of the large animal, the component having an appreciable amount of medicament particles having a size of less than about thirty (30) micrometers.

38. A method of administering a respirable aerosol according to claim 33 wherein the step of providing a conduit comprises the step of providing a conduit with an inlet and sealing surfaces, and the step of inserting the distal end of the conduit into the nostril of the large animal comprises the steps of sealing the nostril of the large animal so that substantially all of the inspiratory airflow through that nostril flows in the inlet, through the lumen and out the outlet of the conduit, and the step of then actuating the aerosol generating device comprises the step of actuating the aerosol generating device upon the large animal's inspiratory airflow.

39. A method of administering a respirable aerosol to a large animal with a nostril, nasal passageway and a nasal diverticulum, such as a horse, comprising the steps of:

(1) providing an aerosol generating device capable of generating a respirable aerosol upon actuation;

(2) providing a conduit comprising:
outer and inner surfaces, a proximal end, and a distal end having an outlet, the inner surfaces defining a lumen extending between the proximal and distal ends and opening to said outer surfaces at said outlet; the conduit having a length which affords locating the outlet in the nasal passageway of the large animal;

(3) connecting the conduit to the aerosol generating device so that the outlet of the conduit is in fluid communication with the aerosol generating device;

(4) inserting the distal end of the conduit into the nostril of the large animal and sufficiently far into the nasal passageway of the large animal to avoid situating the outlet such that the outlet opens in a position that allows passage of the respirable aerosol into the nasal diverticulum of the large animal; and (5) then actuating the aerosol generating device to deliver the respirable aerosol.

40. Apparatus comprising means for administering an aerosol to a large animal having a nasal diverticulum and means for preventing delivery of the aerosol to the nasal diverticulum, the apparatus being adapted for use with an aerosol generating device, the apparatus further comprising:

a conduit having outer surfaces, a proximal end, a distal end having an outlet, and inner surfaces adapted for affording passage of an aerosol generated by an aerosol generating device through the conduit;

the inner surfaces defining a lumen extending between the proximal and distal ends and opening to said outer surfaces at said outlet;

the conduit having a length which affords locating the outlet in the nasal passageway of the large animal;

connecting means comprising surfaces adapted for connecting the conduit to an aerosol generating device, the outlet of the conduit adapted to be placed in fluid communication with an aerosol generating device;

said conduit having a fully inserted position and a size, shape and length that avoids situating said outlet of said conduit in a position that allows passage of aerosol into a nasal diverticulum of a large animal undergoing treatment by means of said outlet of said conduit extending past an animal's diverticulum, wherein aerosol flowing through said conduit exits said outlet at a position distal to an animal's diverticulum.

* * * * *